United States Patent
Kaminsky et al.

(10) Patent No.: US 7,671,222 B2
(45) Date of Patent: Mar. 2, 2010

(54) DIRECT EPOXIDATION PROCESS USING A MIXED CATALYST SYSTEM

(75) Inventors: Mark P. Kaminsky, Media, PA (US); Roger A. Grey, West Chester, PA (US)

(73) Assignee: Lyondell Chemical Technology, L.P., Greenville, DE (US)

(*) Notice: Subject to any disclaimer, the term of this patent is extended or adjusted under 35 U.S.C. 154(b) by 897 days.

(21) Appl. No.: 11/484,906

(22) Filed: Jul. 12, 2006

(65) Prior Publication Data

US 2008/0015372 A1  Jan. 17, 2008

(51) Int. Cl.
*C07D 301/06* (2006.01)
*C07D 301/12* (2006.01)

(52) U.S. Cl. ............................. 549/533; 549/531

(58) Field of Classification Search ........... 549/533, 549/531

See application file for complete search history.

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,666,692 A | 5/1987 | Taramasso et al. | 423/326 |
| 4,833,260 A | 5/1989 | Neri et al. | 549/531 |
| 4,859,785 A | 8/1989 | Bellussi et al. | 549/531 |
| 4,937,216 A | 6/1990 | Clerici et al. | 502/62 |
| 5,859,265 A | 1/1999 | Müller et al. | 549/531 |
| 6,005,123 A | 12/1999 | Dessau et al. | 549/531 |
| 6,008,388 A | 12/1999 | Dessau et al. | 549/531 |
| 6,399,794 B1 | 6/2002 | Hancu | 549/533 |

FOREIGN PATENT DOCUMENTS

| | | |
|---|---|---|
| BE | 1001038 A7 | 6/1989 |
| JP | 4-352771 | 12/1992 |
| WO | WO 98/00413 | 1/1998 |
| WO | WO 2005/077531 A1 | 8/2005 |

*Primary Examiner*—Bernard Dentz
(74) *Attorney, Agent, or Firm*—Kevin M. Carroll

(57) ABSTRACT

The invention is a process for epoxidizing an olefin with hydrogen and oxygen in the presence of a catalyst mixture containing a titanium or vanadium zeolite and a supported catalyst comprising palladium, rhenium and a carrier. The process results in significantly reduced alkane byproduct formed by the hydrogenation of olefin.

17 Claims, No Drawings

DIRECT EPOXIDATION PROCESS USING A MIXED CATALYST SYSTEM

FIELD OF THE INVENTION

This invention relates to an epoxidation process using a mixed catalyst system to produce epoxides from hydrogen, oxygen, and olefins. The mixed catalyst system contains a titanium or vanadium zeolite and a supported catalyst comprising palladium, rhenium and a carrier. Surprisingly, the process results in lower selectivity to undesired alkane byproduct formed by the hydrogenation of olefin compared to similar catalyst systems.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethylbenzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. Nos. 4,833,260, 4,859,785, and 4,937,216, for example, disclose the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

One disadvantage of the described direct epoxidation catalysts is that they are prone to produce non-selective byproducts such as glycols or glycol ethers formed by the ring-opening of the epoxide product or alkane byproduct formed by the hydrogenation of olefin. U.S. Pat. No. 6,008,388 describes a direct olefin epoxidation process in which the selectivity for the reaction of olefin, oxygen, and hydrogen in the presence of a noble metal-modified titanium zeolite is enhanced by the addition of a nitrogen compound such as ammonium hydroxide to the reaction mixture. U.S. Pat. No. 6,399,794 teaches the use of ammonium bicarbonate modifiers to decrease the production of ring-opened byproducts. U.S. Pat. No. 6,005,123 teaches the use of phosphorus, sulfur, selenium or arsenic modifiers such as benzothiophene to decrease the production of propane.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is an olefin epoxidation process that comprises reacting an olefin, hydrogen and oxygen in the presence of a titanium or vanadium zeolite and a supported catalyst. The supported catalyst comprises palladium, rhenium and a carrier. This process surprisingly gives significantly reduced alkane byproduct formed by the hydrogenation of olefin.

DETAILED DESCRIPTION OF THE INVENTION

The process of the invention employs a catalyst mixture that comprises a titanium or vanadium zeolite and a supported catalyst which comprises palladium, rhenium and a carrier. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium or vanadium zeolites are those crystalline materials having a porous molecular sieve structure with titanium or vanadium atoms substituted in the framework. The choice of titanium or vanadium zeolite employed will depend upon a number of factors, including the size and shape of lo the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium or vanadium zeolite such as a zeolite having a structure isomorphous with zeolite beta may be preferred.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst mixture employed in the process of the invention also comprises a supported catalyst that comprises palladium, rhenium and a carrier. The carrier is preferably a porous material. Carriers are well-known in the art. For instance, the carrier can be inorganic oxides, clays, carbon, and organic polymer resins. Preferred inorganic oxides include oxides of Group 2, 3, 4, 5, 6, 13, or 14 elements. Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. The carrier may be a zeolite, but is not a titanium or vanadium zeolite. Preferred organic polymer resins include polystyrene, styrene-divinylbenzene copolymers, crosslinked polyethyleneimines, and polybenzimidizole. Suitable carriers also include organic polymer resins grafted onto inorganic oxide carriers, such as polyethylenimine-silica. Preferred carriers also include carbon. Particularly preferred carriers include carbon, silica, silica-aluminas, titania, zirconia, and niobia.

Preferably, the carrier has a surface area in the range of about 1 to about 700 $m^2/g$, most preferably from about 10 to about 500 $m^2/g$. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the carrier is in the range of about 0.1 μm to about 0.5 inch, more preferably from about 1 μm to about 0.25 inch, and most preferably from about 10 μm to about 1/16 inch. The preferred particle size is dependent upon the type of reactor that is used, for example, larger particle sizes are preferred for a fixed bed reaction. The average pore diameter is typically in the range of about 10 to about 1000 Å, preferably about 20 to about 500 Å, and most preferably about 50 to about 350 Å.

The supported catalyst also contains palladium and rhenium. Typically, the amount of palladium present in the supported catalyst will be in the range of from 0.01 to 20 weight percent, preferably 0.1 to 10 weight percent. The manner in which the palladium is incorporated into the supported catalyst is not considered to be particularly critical. For example, a palladium compound (for example, Pd tetraamine bromide) may be supported on the carrier by impregnation, adsorption, ion-exchange, precipitation, or the like.

There are no particular restrictions regarding the choice of palladium compound or complex used as the source of palladium in the supported catalyst. For example, suitable compounds include the nitrates, sulfates, halides (e.g., chlorides, bromides), carboxylates (e.g. acetate), and amine complexes of palladium.

Similarly, the oxidation state of the palladium is not considered critical. In the case of palladium for instance, the palladium may be in an oxidation state anywhere from 0 to +4 or any combination of such oxidation states. To achieve the desired oxidation state or combination of oxidation states, the palladium compound after being introduced into the supported catalyst may be fully or partially pre-reduced. Satisfactory catalytic performance can, however, be attained without any pre-reduction.

The supported catalyst used in the process of the invention also contains rhenium. The typical amount of rhenium present in the supported catalyst will be in the range of from about 0.01 to 10 weight percent, preferably 0.01 to 2 weight percent. While the choice of rhenium compound used as the rhenium source in the supported catalyst is not critical, suitable compounds include rhenium halides (e.g., chlorides, bromides, iodides), perrhenic acid ($HReO_4$), and ammonium perrhenate ($NH_4ReO_4$). The rhenium may be added to the carrier before, during, or after palladium addition. Any suitable method can be used for the incorporation of rhenium into the supported catalyst. As with palladium addition, the rhenium may be supported on the carrier by impregnation or the like. Incipient wetness and deposition-precipitation techniques may also be used to incorporate the rhenium.

After palladium and rhenium incorporation, the supported catalyst is recovered. Suitable catalyst recovery methods include filtration and washing, rotary evaporation and the like. The supported catalyst is typically dried at a temperature greater than about 50° C. prior to use in epoxidation. The drying temperature is preferably from about 50° C. to about 200° C. The supported catalyst may additionally comprise a binder or the like and may be molded, spray dried, shaped or extruded into any desired form prior to use in epoxidation.

After supported catalyst formation, the supported catalyst may be optionally thermally treated in a gas such as nitrogen, helium, vacuum, hydrogen, oxygen, air, or the like. The thermal treatment temperature is typically from about 50 to about 500° C., preferably from about 100 to about 400° C. It is preferred to thermally treat the supported catalyst in the presence of an oxygen-containing gas at a temperature from about 100 to 400° C., and optionally reduce the supported catalyst in the presence of an hydrogen-containing gas at a temperature from about 100 to 400° C.

The titanium or vanadium zeolite and the supported catalyst may be used in the epoxidation process as a mixture of powders or as a mixture of pellets. In addition, the titanium or vanadium zeolite and supported catalyst may also be pelletized or extruded together prior to use in epoxidation. If pelletized or extruded together, the catalyst mixture may additionally comprise a binder or the like and may be molded, spray dried, shaped or extruded into any desired form prior to use in epoxidation. The weight ratio of titanium or vanadium zeolite: supported catalyst is not particularly critical. However, a titanium or vanadium zeolite: supported catalyst ratio of 0.01-100 (grams of titanium or vanadium zeolite per gram of supported catalyst) is preferred, with a ratio of 1 to 20 more preferred, and a ratio of 5 to 15 most preferred.

The process of the invention comprises contacting an olefin, oxygen, and hydrogen in a solvent in the presence of the catalyst mixture. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2:O_2=1:10$ to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical or subcritical) phase, it is advantageous to work at a pressure of 1-100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, liquid $CO_2$ (in the supercritical or subcritical state), and water. Preferable solvents include water, liquid $CO_2$, and oxygenated hydrocarbons such as alcohols, ethers, esters, ketones, and the like. Preferred oxygenated solvents include lower aliphatic $C_1$-$C_4$ alcohols such as methanol, ethanol, isopropanol, and tert-butanol, or mixtures thereof, and water. Fluorinated alcohols can be used. It is particularly preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, sulfate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

COMPARATIVE EXAMPLE 1

Preparation of Pd/TS-1 Catalyst

Spray dried TS1 (15.778 pounds; 20 wt. % silica binder, 2.1 wt. % Ti, calcined at 550° C.) is added to deionized water (17.89 L) in a 50 liter mixing tank and stirred by an agitator at 500 rpm. The pH of the slurry is adjusted up to 7.0 using 3% aqueous ammonium hydroxide, then tetraammine palladium nitrate aqueous solution (0.166 pounds Pd, diluted to 1 liter) is added over a one-minute period through a subsurface injection, with agitation. The pH of the slurry is maintained at 7.0 during the palladium addition by adding the 3% ammonium hydroxide solution. After palladium addition, the pH is adjusted up to 7.5 with ammonium hydroxide and the slurry is agitated at 30° C. for 60 minutes while maintaining the pH at 7.4. The slurry is filtered and washed (three times with 17 L of deionized water). The solids are then dried in vacuum at 50° C. until a constant weight is obtained, calcined at 300° C. in air for 1 hour, and then treated with 4% $H_2$ in nitrogen for 1 hour. The solids are then re-calcined in air in a muffle furnace at 400° C. for 8 hours (20-110° C. @ 5° C./min; hold 4 hours; ramp 2° C./min to 400° C.; hold 8 hours), cooled to room temperature, then reduced at 400° C. for 8 hours (20-110° C. @ 5° C./min; hold 4 hours; ramp 2° C./min from 110° C. to 400° C.; hold 8 hours) in a quartz tube vertically mounted in an electric tube furnace with 5% hydrogen in nitrogen (300 sccm), and cooled under $H_2/N_2$ flow. An oil filled bubbler is mounted on the vent to prevent air back-streaming into the furnace. Comparative Catalyst 1 is formed. Comparative Catalyst 1 contains 0.1 wt. % palladium, 2.1 wt. % titanium and 44 wt. % silicon.

COMPARATIVE EXAMPLE 2

Preparation of Pd—Re/TS-1

A perrhenic acid solution (4.8975 g of solution, formed by 9.739 g deionized water mixed with 0.0335 g of perrhenic acid from Strem, Re=53 wt. % solution, 99.99% Re-Puratrem) is added dropwise over 25 minutes to Pd/TS-1 (15.07 g, 350° C. calcined/reduced 0.1 wt. % Pd on spray dried TS-1; average 30 micron diameter) while stirring. Once the incipient wetness point is reached, the catalyst is dried in a $N_2$ purged oven at 60° C. for 22 hours, vacuum dried at 60° C. for 4 hours, and then air calcined in a muffle furnace at 400° C. for 8 hours (20-110° C. @ 5° C./min; hold 4 hours; ramp 2° C./min to 400° C.; hold 8 hours). The Pd—Re/TS-1 is then reduced according to the procedure of Comparative Example 1 at 400° C. for 8 hours in a quartz tube vertically mounted in an electric tube furnace with 5% hydrogen in nitrogen (300 sccm) to produce Comparative Catalyst 2. Elemental analysis shows 0.1 wt. % Pd and 0.04 wt. % Re.

EXAMPLE 3

Preparation of Pd/$TiO_2$ and Pd—Re/$TiO_2$ Catalysts

Comparative Catalyst 3A: An $(NH_3)_4Pd(NO_3)_2$ aqueous solution (2.3747 g, of a 5.37 wt. % Pd solution) is added into a 100-mL beaker and mixed with deionized water (7.41 mL). This Pd solution is then added dropwise, over 20-30 minutes, to titanium dioxide (15.1 g of spray dried $TiO_2$, previously calcined to 700° C.). Once the incipient wetness point is reached, the wet $TiO_2$ is dried in a $N_2$ purged oven at 60° C. for 22-23 hours, vacuum dried at 60° C. for 4 hours, and then air calcined in a muffle furnace at 400° C. for 8 hours (20-110° C.

@ 5° C./min; hold 4 hours; ramp 2° C./min to 400° C.; hold 8 hours). The Pd/TiO$_2$ is then reduced according to the procedure of Comparative Example 1 at 400° C. for 8 hours in a quartz tube vertically mounted in an electric tube furnace with 5% hydrogen in nitrogen. Comparative Catalyst 3A shows 0.85 wt. % Pd.

Catalyst 3B: An ammonium perrhenate solution (0.0918 g NH$_4$ReO$_4$, in 4.904 g deionized water) is added dropwise to Comparative Catalyst 3A (Pd/TiO$_2$; 7.5 g) in a 100 mL beaker until the wetness point is reached. The Pd—Re/TiO$_2$ is dried in a N$_2$ purged oven at 60° C. for 22 hours, vacuum dried at 60° C. for 4 hours, air calcined at 110-120° C. for 4 hours, and then reduced according to the procedure of Comparative Example 1 at 400° C. for 8 hours in a quartz tube vertically mounted in an electric tube furnace with 5% hydrogen in nitrogen. The material is then re-calcined in a muffle furnace at 400° C. for 8 hours (20-110° C., at a 5° C./min ramp; hold 4 hours; ramp 2° C./min to 400° C.; hold 8 hours), and re-reduced according to the procedure of Comparative Example 1 at 400° C. for 8 hours in a quartz tube vertically mounted in an electric tube furnace with 5% hydrogen in nitrogen to produce Catalyst 3B. Elemental analysis shows 0.85 wt. % Pd and 0.5 wt. % Re. BET surface area is 44 m$^2$/g.

EXAMPLE 4

Epoxidation Reactions

A 300 cc stainless steel reactor is charged with catalyst (amounts of catalyst are shown in Table 1), methanol (~100 g), and 13 grams of a buffer (0.1 M aqueous ammonium phosphate, pH=6). The reactor is then charged to 300 psig with a feed consisting of 2% hydrogen, 4% oxygen, 5% propylene, 0.5% methane and the balance nitrogen (volume %). The pressure in the reactor is maintained at 300 psig via a backpressure regulator with the feed gases passed continuously through the reactor at 1600 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor, containing 1.5 liters of methanol. The reactor is stirred at 1500 rpm. The reaction mixture is heated to 60° C. and the gaseous effluent is analyzed by an online GC every hour and the liquid analyzed by offline GC at the end of the 18 hour run. Propylene oxide and equivalents ("POE"), which include propylene oxide ("PO"), propylene glycol ("PG"), and propylene glycol methyl ethers (PMs), are produced during the reaction, in addition to propane formed by the hydrogenation of propylene.

The epoxidation results (see Table 2) show that a TS-1 and Pd—Re/TiO$_2$ mixed catalyst shows a significant increase in catalyst activity and propylene selectivity resulting from reduced propane make, compared to Pd/TS-1, Pd—Re/TS-1, or a TS-1 and Pd/TiO$_2$ mixed catalyst.

TABLE 1

Catalyst Amounts for Epoxidation Runs

| Run | Catalyst | Amount Catalyst Added (g) | TS-1 Added (g) |
|---|---|---|---|
| 4A* | 1 | 0.7 | — |
| 4B* | 2 | 0.7 | — |
| 4C* | 3A | 0.07 | 0.63 |
| 4D | 3B | 0.07 | 0.63 |

TABLE 2

Epoxidation Results

| Run | Catalyst Productivity[1] | PO/POE Selectivity (%)[2] | Propylene Selectivity (%)[3] |
|---|---|---|---|
| 4A* | 0.38 | 91 | 73 |
| 4B* | 0.33 | 92 | 78 |
| 4C* | 0.34 | 91 | 84 |
| 4D | 0.4 | 90 | 88 |

[1]Productivity = grams POE produced/gram of catalyst per hour.
[2]PO/POE Selectivity = moles PO/(moles PO + moles propylene glycols) * 100.
[3]Propylene Selectivity = 100 − (moles propane/moles POE + moles propane) * 100.
*Comparative Example

We claim:

1. A process for producing an epoxide comprising reacting an olefin, hydrogen and oxygen in the presence of a titanium or vanadium zeolite and a supported catalyst comprising palladium, rhenium and a carrier, wherein the carrier is not titanium or vanadium zeolite.

2. The process of claim 1 wherein the titanium zeolite is a titanium silicalite.

3. The process of claim 2 wherein the titanium zeolite is TS-1.

4. The process of claim 1 wherein the supported catalyst is comprised of from 0.01 to 10 weight percent palladium.

5. The process of claim 1 wherein the carrier is selected from the group consisting of carbons, titanias, zirconias, niobias, silicas, aluminas, silica-aluminas, tantalum oxides, molybdenum oxides, tungsten oxides, titania-silicas, zirconia-silicas, niobia-silicas, and mixtures thereof.

6. The process of claim 1 wherein the reaction is performed in the presence of a solvent.

7. The process of claim 6 wherein the solvent is an oxygenated solvent.

8. The process of claim 7 wherein the oxygenated solvent is selected from the group consisting of alcohols, ethers, esters, ketones, water, and mixtures thereof.

9. The process of claim 1 wherein the olefin is a $C_2$-$C_6$ olefin.

10. The process of claim 9 wherein the olefin is propylene.

11. The process of claim 6 wherein the reaction is performed in the presence of a buffer.

12. A process for producing propylene oxide comprising reacting propylene, hydrogen and oxygen in an oxygenated solvent in the presence of a titanium silicalite and a supported catalyst comprising palladium, rhenium and a carrier, wherein the carrier is not a titanium or vanadium zeolite.

13. The process of claim 12 wherein the titanium silicalite is TS-1.

14. The process of claim 12 wherein the supported catalyst is comprised of from 0.01 to 10 weight percent palladium.

15. The process of claim 12 wherein the carrier is selected from the group consisting of carbons, titanias, zirconias, niobias, silicas, aluminas, silica-aluminas, tantalum oxides, molybdenum oxides, tungsten oxides, titania-silicas, zirconia-silicas, niobia-silicas, and mixtures thereof.

16. The process of claim 12 wherein the oxygenated solvent is selected from the group consisting of alcohols, ethers, esters, ketones, water, and mixtures thereof.

17. The process of claim 12 wherein the reaction is performed in the presence of a buffer.

* * * * *